(12) United States Patent
Dannhuser et al.

(10) Patent No.: US 9,782,350 B2
(45) Date of Patent: Oct. 10, 2017

(54) COATED DEVICES AND METHODS FOR COATING

(71) Applicant: MEDIZINISCHE HOCHSCHULE HANNOVER, Hannover (DE)

(72) Inventors: Philip Dannhuser, Hannover (DE); Ernst Ungewickell, Hannover (DE)

(73) Assignee: MEDIZINISCHE HOCHSCHULE HANNOVER, Hannover (DE)

( * ) Notice: Subject to any disclaimer, the term of this patent is extended or adjusted under 35 U.S.C. 154(b) by 76 days.

(21) Appl. No.: 14/376,884

(22) PCT Filed: Feb. 6, 2013

(86) PCT No.: PCT/EP2013/052274
§ 371 (c)(1),
(2) Date: Aug. 6, 2014

(87) PCT Pub. No.: WO2013/117560
PCT Pub. Date: Aug. 15, 2013

(65) Prior Publication Data
US 2015/0024206 A1    Jan. 22, 2015

(30) Foreign Application Priority Data
Feb. 6, 2012 (EP) ..................................... 12154004

(51) Int. Cl.
*C07K 14/00* (2006.01)
*A61K 9/127* (2006.01)
*A61K 47/48* (2006.01)
*C07K 14/705* (2006.01)

(52) U.S. Cl.
CPC .......... *A61K 9/1277* (2013.01); *A61K 9/1271* (2013.01); *A61K 47/48276* (2013.01); *A61K 47/48338* (2013.01); *A61K 47/48815* (2013.01); *C07K 14/705* (2013.01); *Y10T 428/2982* (2015.01)

(58) Field of Classification Search
None
See application file for complete search history.

(56) References Cited

PUBLICATIONS

Kalthoff C: et al; Molecular Biology of the Cell; vol. 13, Nov. 1, 2002, p. 4065, Figure 4; p. 4066 Figure 5.
Ford, M. G. J. Nature, vol. 419, Sep. 26, 2002, pp. 361-366, p. 363 right col. line 4—p. 365; figure 6 p. 365; p. 366.
Kirchhausen T. et al.; Annu. Rev. Biochem., vol. 69, Jan. 1, 2000, pp. 699-727.

*Primary Examiner* — Anand Desai
(74) *Attorney, Agent, or Firm* — Grogan, Tuccillo & Vanderleeden, LLP

(57) ABSTRACT

The present invention relates in a first aspect to a method of coating surfaces of substrates with a lattice-like structure. In particular, the present invention relates to an in vitro method of coating surfaces by binding of epsin or a fragment thereof on the surface and, thereafter, binding of a compound forming the lattice like structure, in particular, binding of the clathrin heavy chain, to the epsin bound on the surface, thus, obtaining a coated substrate having a lattice like structure on the surface. In another aspect, the present invention relates to an in vitro method of producing nanometer-sized liposomes having a clathrin structure on its surface. In addition, substrates, like elements or devices, with coated surfaces having a lattice-like structure on the surface are provided obtainable by a method according to the present invention.

11 Claims, 3 Drawing Sheets

Figure3 (A): Electron micrograph of clathrin heavy chain lattices assembled on EpsinΔENTH coated carbon. (B) Electron micrograph of clathrin heavy chain lattices, briefly fixed with 0,1% glutaraldehyde and subsequently incubated with clathrin light chains coupled to gold-nanoparticles. The Gold particles are coordinated by the lattice.

COATED DEVICES AND METHODS FOR COATING

The present invention relates in a first aspect to a method of coating surfaces of substrates with a lattice-like structure. In particular, the present invention relates to an in vitro method of coating surfaces by binding of epsin or a fragment thereof on the surface and, thereafter, binding of a compound forming the lattice like structure, in particular, binding of the clathrin heavy chain, to the epsin bound on the surface, thus, obtaining a coated substrate having a lattice like structure on the surface. In another aspect, the present invention relates to an in vitro method of producing nanometer-sized liposomes having a clathrin structure on its surface. In addition, substrates, like elements or devices, with coated surfaces having a lattice-like structure on the surface are provided obtainable by a method according to the present invention.

BRIEF DESCRIPTION OF THE SEQUENCE LISTING

Incorporated herein by reference in its entirety is a Sequence Listing, comprising SEQ ID NO: 1 to SEQ ID NO: 8. The Sequence Listing is submitted via EFS-Web. The Sequence Listing file is in a computer-readable ASCII file and is entitled 90400001WOUS.txt, was created on Feb. 14, 2017 and is 42,336 bytes in size.

PRIOR ART

Coating is a form of covering that is applied on the surface of an object, usually referred to as the substrate. Typically, coatings are applied to improve surface properties of the substrate, either physical properties, mechanical properties or chemical properties. Coating comprises covering the substrate fully or covering the substrates partially or with specific structures, like lattices having openings. Also in nature coating is known. For example, clathrin is a protein playing a major role in the formation of coated vesicles. Clathrin forms a three-legged structure dubbed "triskelion" composed of three clathrin heavy chains and three light chains in nature. By self assembly of the clathrin triskelia a polyhedral lattice is formed covering or surrounding the substrate, e. g. the vesicle. In nature, these types of proteins are used to build small vesicles in order to transport molecules between cell organelles. That is, clathrin coated vesicles are involved in a number of membrane transport processes, including receptor-mediated endocytosis, recycling of synaptic vesicles and sorting of lysosomal enzymes.

Clathrin coated vesicles occurring in eukaryotic cells possess a lattice like network formed by clathrin triskelia. Clathrin occurs in all eukaryotic cells being composed of the three heavy chains and three light chains. Three heavy chains join at their C-termini to form a stable trimer (triskelion). The light chains interact with the heavy chains without being covalently linked to them. The three heavy chains provide the structural backbone of the clathrin lattice, and the three light chains are thought to regulate the formation and disassembly of the clathrin lattice.

The clathrin heavy chain is composed of various domains. That is, the clathrin heavy chain is composed of the N-terminal domain, followed by the ankle, distal leg, knee, proximal leg, and trimerization domains. The light chains bind primarily to the proximal leg portion of the heavy chain with some interaction near the trimerization domain. While about one third of the light chain interacts with the heavy chain, the remaining portion is free and is available for modification. It is described that the clathrin lattice can form a Buckminster-fullerene-like structures.

For clathrin coated vesicles in cells it is described that clathrin is required to generate nanometer sized vesicles in cells in vivo.

One of the molecules interacting with clathrin is the adaptor protein epsin. Another example is the molecule AP180 that is involved in synaptic vesicle formation. Both compounds promote assembly of clathrin triskelia into Buckminster-fullerene-like structures. Epsin also recruits clathrin to membranes and promotes its assembly. In addition, epsin can bend planar membranes by inserting an amphipatic helix into a monolayer, thus supporting clathrin in the formation of clathrin coated vesicles. For example, Ford M. G. J. et al., Nature, 2002, 419, 361-366, describe the curvature of clathrin-coated pits driven by epsin. Therein, epsin is described as the component responsible for invaginations and curverture of lipid monolayer coated with clathrin heavy and light chains. Of note, clathrin triskelia do not bind directly to membrane, but bind via adaptor proteins to the membrane surface.

As identified, one of these adapter compounds is epsin relevant for budding of clathrin-coated vesicles. That is, epsin contributes to membrane deformation. The epsin molecules are composed of different domains, starting at the N-terminus with a so called ENTH (Epsin N-Terminal Homology) domain that associates with phosphatidylinositol 4,5-bisphospate in biological membranes. The ENTH-domain domain is a structural domain that is found in proteins involved in endocytosis. The ENTH-domain is not only present in epsin but can be found in other proteins involved in membrane trafficking (Epsin 1-3 and EpsinR). The epsin protein is composed further of a middle section containing ubiquitin-interacting motifs and a C-terminal section containing two clathrin binding sites. Thus, epsin represents a suitable adapter for biological membranes and structural compounds, like clathrin.

The ENTH-domain is a domain of approximately 150 amino acid in length, an example thereof is provided with SEQ ID NO: 4 consisting of amino acids 1 to 144 of the sequence of gene bank accession No, NP_476477.

Improving mechanical, physical or chemical properties of substrates represent a permanent problem. In particular, providing substrates, like artificial substrates, in particular artificial biological substrates with suitable coatings to improve mechanical properties remains a problem in the art. Moreover, coating of solid substrates, like inorganic substrates is desired, e.g. for reducing its immunogenic potential. The substrates are typically planar substrates, or having at least planar areas to be coated.

The present invention provides new methods for coating surfaces or substrates with a lattice-like structure having improved mechanical properties, like having improved stability as carrier components, e. g. for drugs. In addition, methods are provided for coating surfaces of substrates whereby said coating includes functionalization of the coating with marker, label, etc., to allow site-directed targeting of the coated substrates.

Moreover, the present invention aims in providing coated elements having improved properties e. g. when use in a subject.

BRIEF DESCRIPTION OF THE PRESENT INVENTION

In a first aspect, the present invention provides an in vitro method for coating surfaces of substrates, typically, a solid and/or planar substrate, in particular solid and planar substrate, with a lattice like structure comprising
   a) binding of epsin, e.g. epsin of SEQ ID NO: 3, or a fragment thereof whereby said fragment is able to interact with the epsin binding domain of clathrin, e.g. epsin absent of the ENTH domain of SEQ ID NO: 4, on a surface of the substrate and
   b) binding of a compound forming a lattice-like structure comprising the clathrin heavy chain comprising the sequence of SEQ ID NO: 1 or a derivative thereof to the epsin or fragment thereof on the surface of the substrate;
   c) obtaining a substrate coated with a lattice-like structure on the surface formed by the compound comprising the clathrin heavy chain.

That is, the present inventors recognised that it is possible to provide coated surfaces of substrates with an artificial lattice-like structure whereby said substrates are preferably elements or devices useful in biotechnical or medicinal application having improved physical and mechanical properties as well as pharmaceutical properties. In addition, based on the lattice like structure on the surface of said substrate, it is possible to modify the surfaces, and, moreover, to functionalize said surfaces. In particular, it is possible to provide an in vitro method for coating surfaces of substrates with the lattice like structure whereby said lattice like structure has preferably a defined pore size.

In another embodiment of the present invention, an in vitro method of producing nanometer-sized liposomes having a clathrin structure on its surface is provided. Said liposomes are in particular liposomes of 70 to 100 nm in size and said method includes incubating the liposomes with at least epsin or a fragment thereof, the clathrin heavy chain in the presence of dynamin and GTP.

In another aspect, the present invention relates to a substrate with coated surfaces obtainable by a method according to the present invention. Said substrate is in particular a liposome or particles having a membrane formed by lipids or other particle forming components. In another aspect, the surfaces of the substrates are composed of metals, carbon, glass or plastic. In addition, substrates having coated surfaces are provided whereby said substrates are useful as filter materials or in the field of catalysts and electrodes.

The substrates having coated surfaces obtainable according to the present invention are particularly useful as coated liposomes in cosmetical and pharmaceutical products or for use as biotemplates. It is preferred that the clathrin structure of the coated substrates is functionalised, e.g. with a marker or label, or, alternatively or in addition, by molecules allowing site-directed targeting of the coated substrates.

BRIEF DESCRIPTION OF THE FIGURES

FIG. 1a shows negatively contrasted liposomes coated with a flat clathrin lattice. FIG. 1c shows a corresponding ultra-thin section of liposomes coated with flat clathrin lattices. In FIG. 1b negatively contrasted membrane buds, generated by coating the liposome surface with the epsin fragment and clathrin can be seen. FIG. 1d represents a corresponding ultra-thin section of a liposome covered with clathrin induced membrane buds. FIG. 1e shows an ultra-thin section of nanometer sized clathrin coated vesicles generated from budded liposomes as shown in 1d.

In FIG. 2A schematic cross section and a top view is shown of a carbon film coated with epsin and, thereon, the clathrin compounds composed of the light chain and heavy chain molecules forming the lattice like structure on the carbon film. FIG. 2B "EM" is an Electron micrograph of negatively stained coated carbon film with an insert enlarging the same.

DETAILED DESCRIPTION OF THE PRESENT INVENTION

Figure 1:
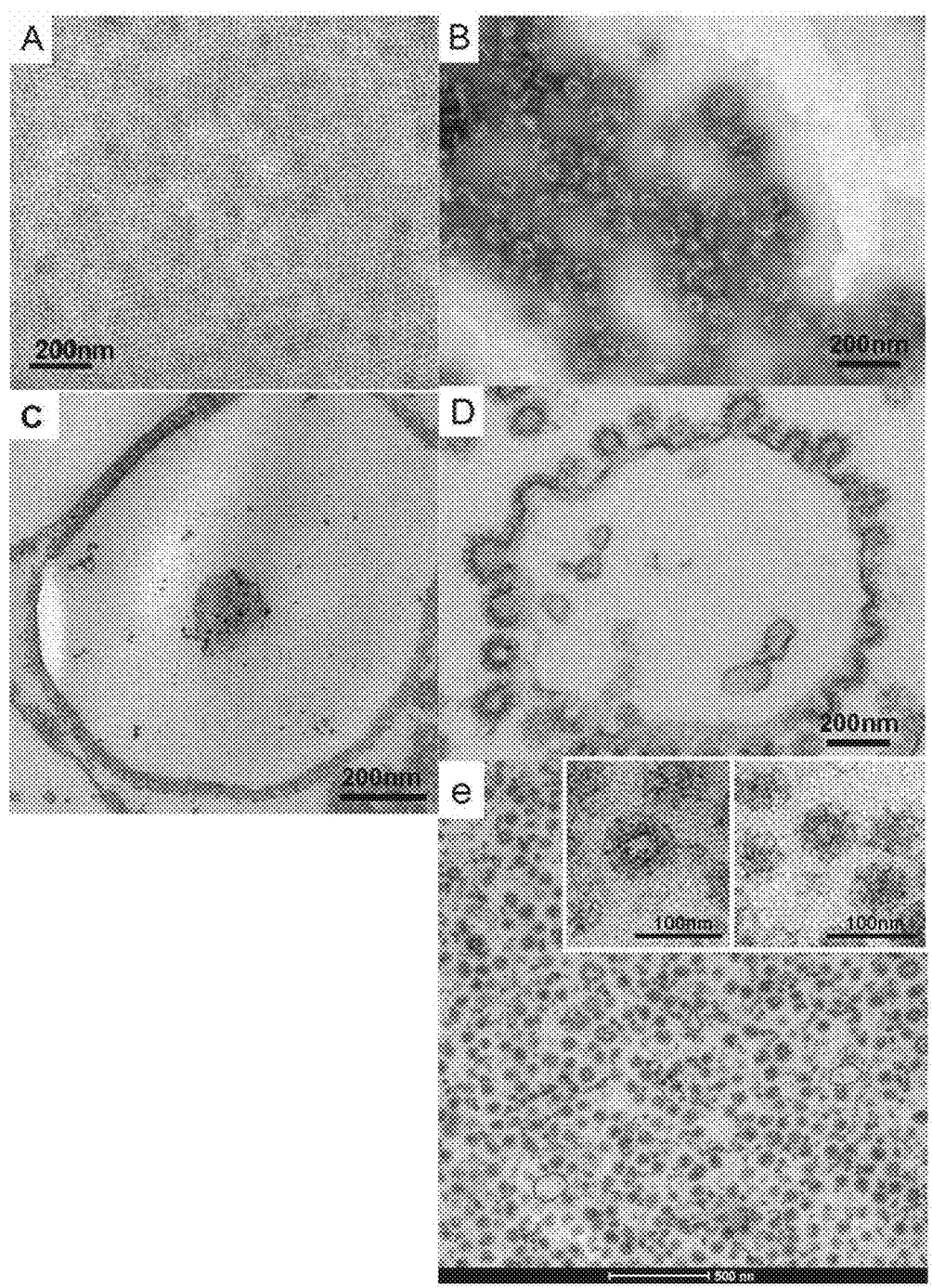
FIG. 1 shows electron micrographs of liposomes coated with clathrin and nanometer sized vesicles generated from larger clathrin coated liposomes according to the present invention. In particular.
Figure 2:
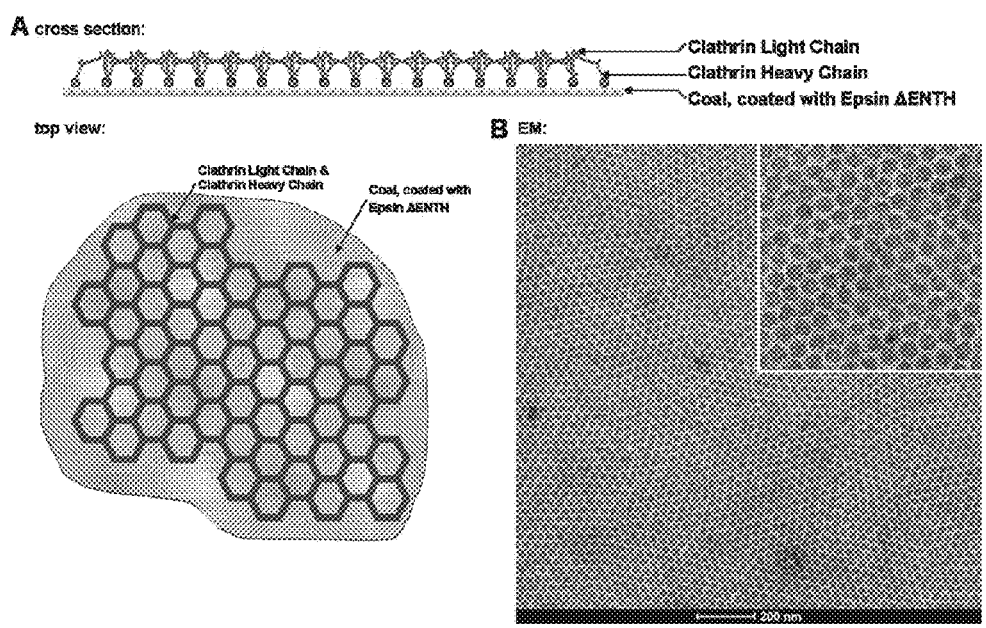
FIG. 2 is an example of coating a carbon substrate. In the present case a carbon film coated with epsin in a first step and, thereafter, with clathrin is shown.
Figure 3:
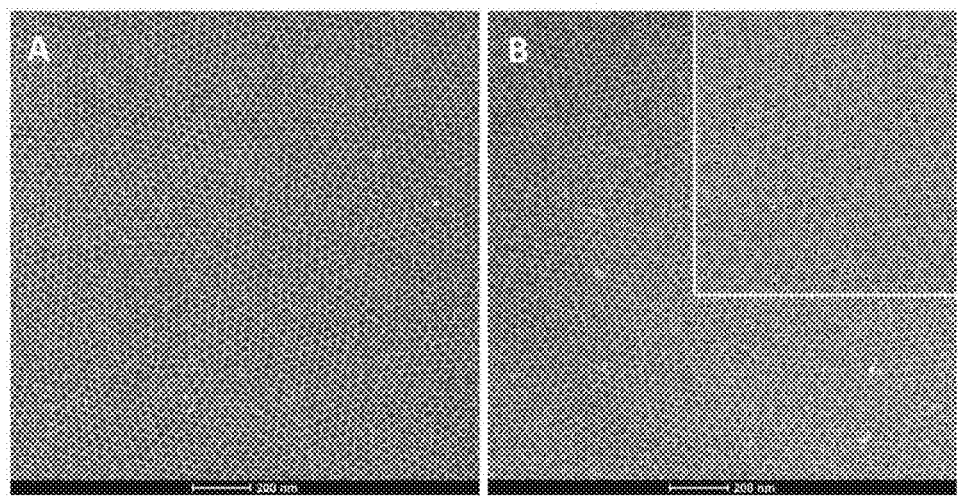
FIG. 3a shows the formation of coated substrates having the lattice-like structure whereby only clathrin heavy chains are bound to the epsin present on the substrate. Thus, binding of the clathrin heavy chains to epsin is sufficient to form the lattice-like structures. Moreover, in FIG. 3b the structure incubated with the clathrin light chain labelled with gold particles is shown demonstrating the possibility to bind label etc to the structure in a coordinated fashion.

In a first aspect, an in vitro method of coating surfaces of solid substrates with a lattice like structure comprising the step of
   a) binding of epsin, like an epsin of SEQ ID NO: 3, or a fragment thereof whereby said fragment is able to interact with the epsin binding domain of clathrin, on a surface of the substrate and
   b) binding of a compound forming a lattice-like structure comprising the clathrin heavy chain comprising the sequence of SEQ ID NO: 1 or a derivative thereof to the epsin or fragment thereof on the surface;
   c) obtaining a substrate coated with a lattice-like structure on the surface formed by the compound comprising the clathrin heavy chain, is provided.

As used herein, the terms "comprising", "comprises" and "comprised of" are synonymous with "including", "includes" or "containing", "contains", and are inclusive or open ended and do not exclude additional, non-recited members, elements or method steps. It will be appreciated that the terms "comprising", "comprises", and "comprised of" as well as "including", "includes", or "containing", "contains" as used herein comprise the terms "consisting of", "consists" and "consists of".

All references cited in the present specification are hereby incorporated by reference in their entirety. In particular, the teachings of all references herein specifically referred to are incorporated by reference.

Unless otherwise defined, all terms used in disclosing the invention, including technical and scientific terms, have the meaning as commonly understood by one of the ordinary skilled in the art to which this invention belongs. By means of further guidance, term definitions are included to better appreciate the teaching of the present invention.

As used herein, the singular forms "a", "an", and "the" include both singular and plural reference unless the context clearly dictates otherwise.

The term "substrate" as used herein refers to any type of elements or devices to be coated. The substrate may be a solid substrate and may be a non-porous or a porous substrate. Examples of suitable substrates include plastic, metal, glass and/or carbon materials or mixtures as well as other inorganic materials thereof. In addition, typical carrier materials, in particular, solid carrier materials, like zeolithe are within the scope of the term "substrate". In addition, substrate comprises biodegradable materials as well as biological materials including liposomes and other forms of particles build up by lipids, surfactants etc.

As used herein, the term "lattice like structure" refers to a structure having a frame work or backbone with openings, e. g. pores or meshes. In particular, the lattice like structure is a structure formed by clathrin as known in the art.

The term "epsin binding domain" refers to the domain described for the clathrin molecules able to bind to the epsin molecule. In particular, the epsin binding domain of the clathrin heavy chain is a sequence comprising the sequence of SEQ ID NO: 1.

As used herein, the term "derivatives" refers to sequences being different to the specific sequence of the SEQ ID NO identified. In particular, the derivatives are polypeptides having amino acid substitutions being conservative substitutions of amino acids as known in the art without deviating from the functionality of the amino acid of the SEQ ID NO provided. For example, a derivative of the epsin binding domain of SEQ ID NO: 1 is an amino acid sequence able to bind to the epsin molecule but having an amino acid sequence not identical with SEQ ID NO: 1. In addition, derivatives include molecules wherein the amino acids are modified amino acids being modified as known in the art. In particular, derivatives include polypeptides or proteins of different species of the respective proteins as identified by reference to a specific SEQ ID NO.

As used herein, the term "fragment thereof" refers to a fragment of the molecule identified having the same activity with respect to the specific functionality identified for the full length molecule. For example, the epsin fragment is a fragment derives from the epsin molecule whereby said fragment is able to interact with the epsin binding domain of clathrin in the same way as described for the epsin molecule.

Moreover, in a preferred embodiment, the binding of epsin to the substrate requires the step of charging the substrate, like charging negatively the substrate, e.g. by glow discharging.

It has been recognised by the present inventors that it is possible to coat in vitro substrates with clathrin, in particular with the clathrin heavy chain only, thus, providing coated substrates having a lattice like structure formed by clathrin on the surface. In particular, the present inventors recognised that for in vitro coating of surfaces of substrates with a lattice like structure, it is sufficient to bind epsin or a fragment thereof whereby said fragment is able to interact with the epsin binding domain of clathrin and, subsequently, binding the clathrin heavy chain, e.g. the peptide of SEQ ID NO: 2 corresponding to gene bank accession No. NP_001139599, to the epsin or fragment thereof bound to the surface of a substrate thereby obtaining a coated substrate having a lattice like structure on the surface formed by the clathrin heavy chains.

It is preferred that the epsin or fragment thereof is an epsin derivative wherein the ENTH moiety according to SEQ ID NO: 4 or a derivative thereof is absent. Further, in an embodiment of the present invention, it is preferred that the epsin or the fragment thereof does not contain a tag, like a GST-tag.

In a preferred embodiment of the present invention, the method includes further the step of binding the clathrin light chain moiety to the clathrin heavy chain moiety. As mentioned above, the clathrin light chain moiety is not necessary to form the lattice like structure but interact with the clathrin heavy chain at the proximal section of the heavy chain. In between binding of the heavy chain to epsin and the subsequent binding of the light chain to the heavy chain, the lattice-like structures of epsin bound to the substrate and the heavy chain may be chemically stabilized by suitable means.

In a preferred embodiment, the clathrin light chain, e.g. of SEQ ID NO: 5 or SEQ ID NO: 6 corresponding to gene bank accession No. ID P04975 or XP_003123718, respectively, is functionalised. That is, a preferred embodiment relates to a substrates being coated on the surface with functionalised clathrin structures wherein the light chain of clathrin is functionalised by a component selected from the group consisting of label, marker, enzyme, protein binding sequence for metals, proteins other than clathrin, active drugs or prodrugs.

As used herein, the term "label" refers to a label capable of producing, either directly or indirectly, a detectable signal. For example, the label may be a radioisotope, a fluorescent (fluorophore), or chemiluminescent (lumiphore) compound, an enzyme, an imaging agent, magnetic or paramagnetic labels, or a metal ion.

Further, as used herein, the term "marker" refers to a component allowing detecting directly or indirectly the molecules having said marker as one component. The marker may be a label as defined above or may be a specific sequence of a chemical entity including nucleic acid sequences and amino acid sequences allowing detection of the same with suitable measures known in the art.

That is, the clathrin structures which may be functionalized include preferably functionalized light chain of clathrin whereby functionalization is effected by covalently or non covalently binding of a label, marker, enzyme, protein, binding sequence for metals, proteins other then clathrin, active drugs or prodrugs as well as nucleic acid sequences. Said marker or label components may be detected with suitable means including secondary antibodies fluorescent components etc.

Further, as used herein, the term biotemplates refers to a structure generated with biomaterial that is used as matrix for the association of non-biological successor materials.

In another embodiment of the present invention, the substrates are a plastic, metal, glass, or carbon material. Typical examples of substrates are medicinal or pharmaceutical substrates or biotemplates. For example, the substrate is a medicinal or pharmaceutical device. Alternatively, the substrate is a liposome or biodegradable particles or fibers. Fibers can be coated with clathrin generating regular nanometer sized tubes with carbon nanotube-like structures. That is, according to a preferred embodiment, the method of coating surfaces of substrate is a method of coating liposomes or biodegradable membranes in vitro.

In a preferred embodiment, the method according to the present invention comprises the step of incubating and binding of the compound epsin, comprising the clathrin binding domain, preferably, the clathrin heavy chain, sequentially, simultaneously or subsequently together with the molecule dynamin, e.g. a peptide of SEQ ID NO: 7 corresponding to gene bank accession No. AAH50279 or SEQ ID NO: 8 corresponding to gene bank accession No. XP_003122242, respectively, and, optionally, GTP as detailed below, dynamin is a GTPase molecule which allows release of nanometer sized clathrin coated vesicles from larger liposomes.

That is, in another embodiment of the present invention an in vitro method of producing nanometer sized liposomes having a clathrin structure on its surface, in particular, for the production of liposomes, having a size of 70 to 100 nm is provided. Said in vitro method comprises the steps of incubating liposomes with epsin or fragments thereof whereby said fragment is able to interact with the epsin binding domain of the clathrin heavy chain; incubating said liposomes having epsin or fragments thereof on its surface with at least the clathrin-binding domain and the clathrin heavy chain in the presence of dynamin and, optionally, GTP; obtaining nanometer-sized liposomes having a clathrin structure on its surface.

The combination of epsin, clathrin, dynamin and GTP allows the production of the nanometer sized liposomes having a defined size range.

In another aspect, the present invention relates to a substrate with coated surfaces obtainable by a method according to the present invention. The substrate is characterized by having a lattice-like structure coated on the surface whereby said lattice-like structure is preferably formed by clathrin triskelia as describes herein. Said clathrin triskelia allow the formation of a defined lattice-like structure with defined openings. Typically, the surface of the substrate is planar or has planar areas.

It is preferred, that the substrate having a coated surface according to the present invention is a substrate having a surface according to the present invention is a substrate having a surface of liposomes, metals, carbon, glass, plastic or mixtures thereof.

That is, the substrates according to the present invention having a coated surface as defined herein are suitable for use in various fields including medicinal or pharmaceutical fields. For example, the substrate may be modified having a reduced or specific immunogenicity compared to the uncoated substrate. Thus, these coated substrates are suitable as medicinal devices, in particular, implants or pharmaceutical carriers. In addition, coated substrates are useful in catalyst and electrodes as well as filter materials, in particular, as molecular filter.

In case the coated substrates are used in the field of catalyst or molecular filters, the substrate is preferably at least partially degradable. For example, in case of coated liposomes, the components forming the liposomes may be removed by suitable means, thus, remaining the clathrin structure as a cage-like structure. Any components present in the liposomes having a larger size than the size of the opening of the lattice like structure formed preferably by the clathrin molecules (for example, having a size of larger than 40 nm) remain in the cage structure formed by the clathrin coating. Thus, substrates and products of catalysts, present in the cage structure, e. g. enzymes or anorganic catalysts, enter and leave the cage structure while the catalytic element remain in the structure. Alternatively, the substrate may be any biodegradable material, e. g. polylactic particles etc., known to the person skilled in the art. When introducing the substrate into an object, the material is degraded, thus, releasing any components present in or enveloped by the biodegradable material.

In another aspect, the substrates are particularly useful as carriers in cosmetical and pharmaceutical products for use as biotemplates, in particular, biotemplates in form of liposomes or other biodegradable material having functionalized clathrin structures. In particular, when the light chain of the clathrin is functionalized, e. g. with a structure allowing site directed targeting; the coated substrates allow the site directed delivery of compounds, e. g. drugs or prodrugs. The skilled person is well as whereof suitable compounds therefore.

For example in case of coated liposomes, the coating stabilizes the liposomes, thus prevents fusion of liposomes with each other and increases the shelf life. In addition, the coating allows changing immunogenicity of the substrates.

In addition, in particular, in the field of liposomes and its medicinal use, the coated liposomes according to the present invention allows to provide carrier structures having improved stability with modifiable immunogenicity. Moreover, the coating allows obtaining liposomes having a defined size and shape as well as having an enlarged surface. In addition, modification of the surface of the liposomes is possible, e. g. by binding of target structures as well as marker or labels. Moreover, due to the more uniform size and character of the coated liposomes, the drugs or prodrugs incorporated therein may be allow a more defined and controlled dosage thereof.

Moreover, coating of substrates other than liposomes, for example, carbon surfaces or metal surfaces allow to reduce immunogenicity thereof when incorporated into a subject, e. g. in form of an implant. Moreover, the properties of the surfaces of the substrate may be changed by coating thereof.

In the following the invention will be described further by examples without limiting the same thereto.

Example 1

Coating of Carbon Film

Carbon film having a thickness of 10 nm were coated first with the fragment H6-epsin144-575 (H6=hexahistidine) or, alternatively, with epsin 1 (or H6-epsin). The coating was carried out non-covalently by glow discharge of the carbon film as described below. The coating of said fragment or the protein may also be covalent as described before (Debasis S., and Sarkar A., Chem. Soc. Rev., 2011, 40, 2567-2592.

Brief Description of the Non-Covalent Coating Procedure:

1. Ionisation of the surface by glow discharge (Leybold-Hereaus Combitron CM30: $10^{-1}$ Torr, Balzers BSV 080 Evaporation Control: Discharge 4×0.5 s, 13 mA)
2. Incubation of the surface with at least 0.93 pmol/mm$^2$ of epsin fragment or epsin in HEPES buffer (25 mM HEPES ((4-(2-hydroxyethyl)-1-piperazineethanesulfonic acid, 125 mM potassium acetate, 5 mM magnesium acetate; pH 7.2, room temperature) for 30 minutes
3. Rinsing of the epsin-coated surface with HEPES-buffer to remove unbound epsin.
4. Incubation of the epsin-coated surface with 5.2 pmol/mm$^2$ clathrin (at a minimal concentration of about 0.026 µM) in HEPES Buffer+BSA (25 mM HEPES, 125 mM potassium acetate, 5 mM magnesium acetate, 0.1% (m/v)+Bovine Serum Albumin, pH 7.2, room temperature) for 30 minutes. If necessary a successive incubation of the surface with clathrin in solution may be applied to saturate the surface.
5. Rinsing of the epsin-coated surface to remove unbound clathrin.

Example 2

Coating of Liposomes and Production of Nanometer Sized Clathrin Coated Vesicles

Coating of Liposomes:
1. Incubation of liposomes, enriched with DGS-Ni-NTA (1,2-dioleoyl-sn-glycero-3-[(N-(5-amino-1-carboxypentyl)iminodiacetic acid)succinyl] (nickel salt)) 5% (w/w), with H6-Epsin 144-575 (1.8 µM).
2. Removal of unbound protein by centrifugation.
3. Incubation of the resuspended liposomes with clathrin (0.7 µM). For the generation of flat clathrin lattices, all incubation steps are carried out at 4° C. For the generation of budded membrane coated with clathrin lattices, all incubation steps are carried out at room temperature (about 23-37° C.).

4. Removal of unbound clathrin by centrifugation at 4° C. and resuspension of the liposomes.

Production of Nanometer Sized Clathrin Coated Vesicles:
1. Incubation of liposomes, enriched with DGS-Ni-NTA (5% (w/w)), with H6-Epsin 144-575 (18 μM).
2. Removal of unbound protein by centrifugation.
3. Incubation of the resuspended liposomes with clathrin (0.43 μM) and dynamin (0.31 μM) simultaneously for 30 Minuten at 4° C.
4. To release the vesicles, the coated liposomes are incubated at 37° C. for 30 minutes in the presence of GTP (2 mM).
5. Nanometer sized clathrin coated vesicles and residual larger liposomes can be separated by centrifugation.

Example 3

Coating of a Carbon Film with Clathrin Heavy Chain and Labelling with Modified Clathrin Light Chains.

Carbon film having a thickness of 10 nm were coated first with the fragment H6-epsin144-575 (H6=hexahistidine) or, alternatively, with epsin 1 (or H6-epsin). The coating was carried out non-covalently by glow discharge of the carbon film as described below. The coating of said fragment or the protein may also be covalent as described before (Debasis S., and Sarkar A., Chem. Soc. Rev., 2011, 40, 2567-2592).

Brief Description of the Non-Covalent Coating Procedure:
1. Ionisation of the surface by glow discharge (Leybold-Hereaus Combitron CM30: $10^{-1}$ Torr, Balzers BSV 080 Evaporation Control: Discharge 4×0.5 s, 13 mA).
2. Incubation of the surface with at least 0.93 pmol/mm$^2$ of epsin fragment or epsin in HEPES buffer (25 mM HEPES ((4-(2-hydroxyethyl)-1-piperazineethanesulfonic acid, 125 mM potassium acetate, 5 mM magnesium acetate; pH 7.2, room temperature) for 30 minutes.
3. Rinsing of the epsin-coated surface with HEPES-buffer to remove unbound epsin.
4. Incubation of the epsin-coated surface with 1.3 pmol/mm$^2$ clathrin heavy chain (at a minimal concentration of about 0.048 μM) in HEPES buffer+BSA (25 mM HEPES, 125 mM potassium acetate, 5 mM magnesium acetate, 0.1% (m/v)+Bovine Serum Albumin, pH 7.2, room temperature) for 30 minutes. If necessary a successive incubation of the surface with clathrin in solution may be applied to saturate the surface.
5. Rinsing of the epsin-coated surface to remove unbound clathrin heavy chain.
6. Brief fixation of the clathrin heavy chain lattice with 0.1% glutaraldehyde in HEPES buffer (see above) for 10 minutes at room temperature.
7. Rinsing of the coated surface to remove excess fixative.
8. Incubation of the coated surface with Clathrin light chains coupled to 5 nm gold particles (Productnr. EMGC5, Plano GmbH, Wetzlar, Germany) for 30 minutes in HEPES buffer+BSA+ammonium sulfate (25 mM HEPES, 125 mM potassium acetate, 10 mM ammonium sulphate, 5 mM magnesium acetate, 0.1% (m/v)+Bovine Serum Albumin, pH 7.2, room temperature) at room temperature. Coupling of light chains and gold particles was carried out before the incubation with the heavy chain lattice, according to the manufacturers instructions.
9. Rinsing of the coated surface to remove excess protein and gold particles.

What is claimed is:

1. An in-vitro method of coating surfaces of solid substrates with a lattice-like structure comprising the steps of:
    binding epsin, or a fragment thereof, on a surface of a solid substrate, whereby said epsin or fragment is able to interact with an epsin binding domain of clathrin;
    binding a compound having an epsin binding domain to the epsin or fragment thereof on the surface to form a lattice-like structure, the epsin binding domain includes a clathrin heavy chain comprising SEQ ID NO: 1 or a derivative thereof; and
    obtaining the substrate coated with the lattice-like structure on the surface formed by the compound comprising the epsin binding domain of the clathrin heavy chain.

2. The method of claim 1 wherein the lattice like structure is a clathrin triskelia and the compound comprises at least the full length clathrin heavy chain comprising the peptide of SEQ ID NO: 2.

3. The method of claim 1 further comprising the step of:
    binding of a clathrin light chain comprising the peptide of SEQ ID NO: 5 or SEQ ID NO: 6, or a fragment thereof, to the full length clathrin heavy chains.

4. The method of claim 3 wherein the clathrin light chain is functionalised.

5. The method of claim 1 wherein the epsin or fragment thereof is an epsin derivative wherein the ENTH moiety of according to SEQ ID NO: 4, or a derivative thereof, is absent.

6. The method of claim 4 wherein the light chain of clathrin is functionalised by at least one component selected from the group consisting of label, marker, enzyme, protein binding sequence for metals, proteins other than clathrin, nucleic acids, active drugs or prodrugs, or combinations thereof.

7. The method according to claim 1, wherein the surface of the solid substrate comprises an inorganic material including at least one of plastic, metal, glass, carbon.

8. The method according to claim 1 further comprising the step of charging the surface of the substrate prior to binding the epsin or fragment thereof, including negatively charging the surface of the substrate by glow discharge before binding of epsin or a fragment thereof.

9. The method according to claim 1, wherein the solid substrate is a medicinal or pharmaceutical device or carrier.

10. The method according to claim 1 further comprising the steps of sequentially, simultaneously or subsequently incubating and binding the clathrin heavy chain together with dynamin according to SEQ ID NO: 7 or SEQ ID NO: 8, or an isoform thereof, and, optionally, GTP.

11. A solid substrate with coated surfaces obtainable by a method according to claim 1 wherein the surfaces are metals, carbon, glass, or plastic.

* * * * *

UNITED STATES PATENT AND TRADEMARK OFFICE
CERTIFICATE OF CORRECTION

PATENT NO. : 9,782,350 B2  
APPLICATION NO. : 14/376884  
DATED : October 10, 2017  
INVENTOR(S) : Philip Dannhauser and Ernst Ungewickell Page 1 of 1

It is certified that error appears in the above-identified patent and that said Letters Patent is hereby corrected as shown below:

On the Title Page

Item (72):  
FIRST INVENTOR'S NAME is spelled incorrectly. It's currently spelled PHILIP DANNHUSER.  
The correct spelling of the Inventor's name is Philip DANNHAUSER.

Signed and Sealed this  
Fourteenth Day of August, 2018

Andrei Iancu  
*Director of the United States Patent and Trademark Office*

SEQUENCE LISTING

<160> NUMBER OF SEQ ID NOS: 8

<210> SEQ ID NO 1
<211> LENGTH: 350
<212> TYPE: PRT
<213> ORGANISM: sus scrofa

<400> SEQUENCE: 1

```
Met Ala Gln Ile Leu Pro Ile Arg Phe Gln Glu His Leu Gln Leu Gln
1               5                   10                  15

Asn Leu Gly Ile Asn Pro Ala Asn Ile Gly Phe Ser Thr Leu Thr Met
            20                  25                  30

Glu Ser Asp Lys Phe Ile Cys Ile Arg Glu Lys Val Gly Glu Gln Ala
        35                  40                  45

Gln Val Val Ile Ile Asp Met Asn Asp Pro Ser Asn Pro Ile Arg Arg
    50                  55                  60

Pro Ile Ser Ala Asp Ser Ala Ile Met Asn Pro Ala Ser Lys Val Ile
65                  70                  75                  80

Ala Leu Lys Ala Gly Lys Thr Leu Gln Ile Phe Asn Ile Glu Met Lys
                85                  90                  95

Ser Lys Met Lys Ala His Thr Met Thr Asp Asp Val Thr Phe Trp Lys
            100                 105                 110
```

```
Trp Ile Ser Leu Asn Thr Val Ala Leu Val Thr Asp Asn Ala Val Tyr
            115                 120                 125

His Trp Ser Met Glu Gly Glu Ser Gln Pro Val Lys Met Phe Asp Arg
        130                 135                 140

His Ser Ser Leu Ala Gly Cys Gln Ile Ile Asn Tyr Arg Thr Asp Ala
145                 150                 155                 160

Lys Gln Lys Trp Leu Leu Thr Gly Ile Ser Ala Gln Gln Asn Arg
                165                 170                 175

Val Val Gly Ala Met Gln Leu Tyr Ser Val Asp Arg Lys Val Ser Gln
                180                 185                 190

Pro Ile Glu Gly His Ala Ala Ser Phe Ala Gln Phe Lys Met Glu Gly
            195                 200                 205

Asn Ala Glu Glu Ser Thr Leu Phe Cys Phe Ala Val Arg Gly Gln Ala
        210                 215                 220

Gly Gly Lys Leu His Ile Ile Glu Val Gly Thr Pro Pro Thr Gly Asn
225                 230                 235                 240

Gln Pro Phe Pro Lys Lys Ala Val Asp Val Phe Phe Pro Pro Glu Ala
                245                 250                 255

Gln Asn Asp Phe Pro Val Ala Met Gln Ile Ser Glu Lys His Asp Val
            260                 265                 270

Val Phe Leu Ile Thr Lys Tyr Gly Tyr Ile His Leu Tyr Asp Leu Glu
        275                 280                 285

Thr Gly Thr Cys Ile Tyr Met Asn Arg Ile Ser Gly Glu Thr Ile Phe
        290                 295                 300

Val Thr Ala Pro His Glu Ala Thr Ala Gly Ile Ile Gly Val Asn Arg
305                 310                 315                 320

Lys Gly Gln Val Leu Ser Val Cys Val Glu Glu Asn Ile Ile Pro
                325                 330                 335

Tyr Ile Thr Asn Val Leu Gln Asn Pro Asp Leu Ala Leu Arg
            340                 345                 350

<210> SEQ ID NO 2
<211> LENGTH: 1675
<212> TYPE: PRT
<213> ORGANISM: sus scrofa

<400> SEQUENCE: 2

Met Ala Gln Ile Leu Pro Ile Arg Phe Gln Glu His Leu Gln Leu Gln
1               5                   10                  15

Asn Leu Gly Ile Asn Pro Ala Asn Ile Gly Phe Ser Thr Leu Thr Met
                20                  25                  30

Glu Ser Asp Lys Phe Ile Cys Ile Arg Glu Lys Val Gly Glu Gln Ala
            35                  40                  45

Gln Val Val Ile Ile Asp Met Asn Asp Pro Ser Asn Pro Ile Arg Arg
        50                  55                  60

Pro Ile Ser Ala Asp Ser Ala Ile Met Asn Pro Ala Ser Lys Val Ile
65                  70                  75                  80

Ala Leu Lys Ala Gly Lys Thr Leu Gln Ile Phe Asn Ile Glu Met Lys
                85                  90                  95

Ser Lys Met Lys Ala His Thr Met Thr Asp Asp Val Thr Phe Trp Lys
            100                 105                 110

Trp Ile Ser Leu Asn Thr Val Ala Leu Val Thr Asp Asn Ala Val Tyr
        115                 120                 125

His Trp Ser Met Glu Gly Glu Ser Gln Pro Val Lys Met Phe Asp Arg
    130                 135                 140
```

-continued

```
His Ser Ser Leu Ala Gly Cys Gln Ile Ile Asn Tyr Arg Thr Asp Ala
145                 150                 155                 160

Lys Gln Lys Trp Leu Leu Leu Thr Gly Ile Ser Ala Gln Gln Asn Arg
            165                 170                 175

Val Val Gly Ala Met Gln Leu Tyr Ser Val Asp Arg Lys Val Ser Gln
        180                 185                 190

Pro Ile Glu Gly His Ala Ala Ser Phe Ala Gln Phe Lys Met Glu Gly
    195                 200                 205

Asn Ala Glu Glu Ser Thr Leu Phe Cys Phe Ala Val Arg Gly Gln Ala
210                 215                 220

Gly Gly Lys Leu His Ile Ile Glu Val Gly Thr Pro Thr Gly Asn
225                 230                 235                 240

Gln Pro Phe Pro Lys Lys Ala Val Asp Val Phe Phe Pro Pro Glu Ala
            245                 250                 255

Gln Asn Asp Phe Pro Val Ala Met Gln Ile Ser Glu Lys His Asp Val
        260                 265                 270

Val Phe Leu Ile Thr Lys Tyr Gly Tyr Ile His Leu Tyr Asp Leu Glu
    275                 280                 285

Thr Gly Thr Cys Ile Tyr Met Asn Arg Ile Ser Gly Glu Thr Ile Phe
290                 295                 300

Val Thr Ala Pro His Glu Ala Thr Ala Gly Ile Ile Gly Val Asn Arg
305                 310                 315                 320

Lys Gly Gln Val Leu Ser Val Cys Val Glu Glu Asn Ile Ile Pro
            325                 330                 335

Tyr Ile Thr Asn Val Leu Gln Asn Pro Asp Leu Ala Leu Arg Met Ala
        340                 345                 350

Val Arg Asn Asn Leu Ala Gly Ala Glu Glu Leu Phe Ala Arg Lys Phe
    355                 360                 365

Asn Ala Leu Phe Ala Gln Gly Asn Tyr Ser Glu Ala Ala Lys Val Ala
370                 375                 380

Ala Asn Ala Pro Lys Gly Ile Leu Arg Thr Pro Asp Thr Ile Arg Arg
385                 390                 395                 400

Phe Gln Ser Val Pro Ala Gln Pro Gly Gln Thr Ser Pro Leu Leu Gln
            405                 410                 415

Tyr Phe Gly Ile Leu Leu Asp Gln Gly Gln Leu Asn Lys Tyr Glu Ser
        420                 425                 430

Leu Glu Leu Cys Arg Pro Val Leu Gln Gln Gly Arg Lys Gln Leu Leu
    435                 440                 445

Glu Lys Trp Leu Lys Glu Asp Lys Leu Glu Cys Ser Glu Glu Leu Gly
450                 455                 460

Asp Leu Val Lys Ser Val Asp Pro Thr Leu Ala Leu Ser Val Tyr Leu
465                 470                 475                 480

Arg Ala Asn Val Pro Asn Lys Val Ile Gln Cys Phe Ala Glu Thr Gly
            485                 490                 495

Gln Val Gln Lys Ile Val Leu Tyr Ala Lys Lys Val Gly Tyr Thr Pro
        500                 505                 510

Asp Trp Ile Phe Leu Leu Arg Asn Val Met Arg Ile Ser Pro Asp Gln
    515                 520                 525

Gly Gln Gln Phe Ala Gln Met Leu Val Gln Asp Glu Glu Pro Leu Ala
530                 535                 540

Asp Ile Thr Gln Ile Val Asp Val Phe Met Glu Tyr Asn Leu Ile Gln
545                 550                 555                 560
```

```
Gln Cys Thr Ala Phe Leu Leu Asp Ala Leu Lys Asn Asn Arg Pro Ser
            565                 570                 575
Glu Gly Pro Leu Gln Thr Arg Leu Leu Glu Met Asn Leu Met His Ala
        580                 585                 590
Pro Gln Val Ala Asp Ala Ile Leu Gly Asn Gln Met Phe Thr His Tyr
            595                 600                 605
Asp Arg Ala His Ile Ala Gln Leu Cys Glu Lys Ala Gly Leu Leu Gln
        610                 615                 620
Arg Ala Leu Glu His Phe Thr Asp Leu Tyr Asp Ile Lys Arg Ala Val
625                 630                 635                 640
Val His Thr His Leu Leu Asn Pro Glu Trp Leu Val Asn Tyr Phe Gly
            645                 650                 655
Ser Leu Ser Val Glu Asp Ser Leu Glu Cys Leu Arg Ala Met Leu Ser
            660                 665                 670
Ala Asn Ile Arg Gln Asn Leu Gln Ile Cys Val Gln Val Ala Ser Lys
            675                 680                 685
Tyr His Glu Gln Leu Ser Thr Gln Ser Leu Ile Glu Leu Phe Glu Ser
        690                 695                 700
Phe Lys Ser Phe Glu Gly Leu Phe Tyr Phe Leu Gly Ser Ile Val Asn
705                 710                 715                 720
Phe Ser Gln Asp Pro Asp Val His Phe Lys Tyr Ile Gln Ala Ala Cys
            725                 730                 735
Lys Thr Gly Gln Ile Lys Glu Val Glu Arg Ile Cys Arg Glu Ser Asn
            740                 745                 750
Cys Tyr Asp Pro Glu Arg Val Lys Asn Phe Leu Lys Glu Ala Lys Leu
        755                 760                 765
Thr Asp Gln Leu Pro Leu Ile Ile Val Cys Asp Arg Phe Asp Phe Val
        770                 775                 780
His Asp Leu Val Leu Tyr Leu Tyr Arg Asn Asn Leu Gln Lys Tyr Ile
785                 790                 795                 800
Glu Ile Tyr Val Gln Lys Val Asn Pro Ser Arg Leu Pro Val Val Ile
            805                 810                 815
Gly Gly Leu Leu Asp Val Asp Cys Ser Glu Asp Val Ile Lys Asn Leu
            820                 825                 830
Ile Leu Val Val Arg Gly Gln Phe Ser Thr Asp Glu Leu Val Ala Glu
        835                 840                 845
Val Glu Lys Arg Asn Arg Leu Lys Leu Leu Leu Pro Trp Leu Glu Ala
        850                 855                 860
Arg Ile His Glu Gly Cys Glu Glu Pro Ala Thr His Asn Ala Leu Ala
865                 870                 875                 880
Lys Ile Tyr Ile Asp Ser Asn Asn Asn Pro Glu Arg Phe Leu Arg Glu
            885                 890                 895
Asn Pro Tyr Tyr Asp Ser Arg Val Val Gly Lys Tyr Cys Glu Lys Arg
        900                 905                 910
Asp Pro His Leu Ala Cys Val Ala Tyr Glu Arg Gly Gln Cys Asp Leu
        915                 920                 925
Glu Leu Ile Asn Val Cys Asn Glu Asn Ser Leu Phe Lys Ser Leu Ser
        930                 935                 940
Arg Tyr Leu Val Arg Arg Lys Asp Pro Glu Leu Trp Gly Ser Val Leu
945                 950                 955                 960
Leu Glu Ser Asn Pro Tyr Arg Arg Pro Leu Ile Asp Gln Val Val Gln
            965                 970                 975
```

```
Thr Ala Leu Ser Glu Thr Gln Asp Pro Glu Val Ser Val Thr Val
            980                 985                 990

Lys Ala Phe Met Thr Ala Asp Leu Pro Asn Glu Leu Ile Glu Leu Leu
        995                 1000                1005

Glu Lys Ile Val Leu Asp Asn Ser Val Phe Ser Glu His Arg Asn
        1010                1015                1020

Leu Gln Asn Leu Leu Ile Leu Thr Ala Ile Lys Ala Asp Arg Thr
        1025                1030                1035

Arg Val Met Glu Tyr Ile Asn Arg Leu Asp Asn Tyr Asp Ala Pro
        1040                1045                1050

Asp Ile Ala Asn Ile Ala Ile Ser Asn Glu Leu Phe Glu Glu Ala
        1055                1060                1065

Phe Ala Ile Phe Arg Lys Phe Asp Val Asn Thr Ser Ala Val Gln
        1070                1075                1080

Val Leu Ile Glu His Ile Gly Asn Leu Asp Arg Ala Tyr Glu Phe
        1085                1090                1095

Ala Glu Arg Cys Asn Glu Pro Ala Val Trp Ser Gln Leu Ala Lys
        1100                1105                1110

Ala Gln Leu Gln Lys Gly Met Val Lys Glu Ala Ile Asp Ser Tyr
        1115                1120                1125

Ile Lys Ala Asp Asp Pro Ser Ser Tyr Met Glu Val Val Gln Ala
        1130                1135                1140

Ala Asn Thr Ser Gly Asn Trp Glu Glu Leu Val Lys Tyr Leu Gln
        1145                1150                1155

Met Ala Arg Lys Lys Ala Arg Glu Ser Tyr Val Glu Thr Glu Leu
        1160                1165                1170

Ile Phe Ala Leu Ala Lys Thr Asn Arg Leu Ala Glu Leu Glu Glu
        1175                1180                1185

Phe Ile Asn Gly Pro Asn Asn Ala His Ile Gln Gln Val Gly Asp
        1190                1195                1200

Arg Cys Tyr Asp Glu Lys Met Tyr Asp Ala Ala Lys Leu Leu Tyr
        1205                1210                1215

Asn Asn Val Ser Asn Phe Gly Arg Leu Ala Ser Thr Leu Val His
        1220                1225                1230

Leu Gly Glu Tyr Gln Ala Ala Val Asp Gly Ala Arg Lys Ala Asn
        1235                1240                1245

Ser Thr Arg Thr Trp Lys Glu Val Cys Phe Ala Cys Val Asp Gly
        1250                1255                1260

Lys Glu Phe Arg Leu Ala Gln Met Cys Gly Leu His Ile Val Val
        1265                1270                1275

His Ala Asp Glu Leu Glu Glu Leu Ile Asn Tyr Tyr Gln Asp Arg
        1280                1285                1290

Gly Tyr Phe Glu Glu Leu Ile Thr Met Leu Glu Ala Ala Leu Gly
        1295                1300                1305

Leu Glu Arg Ala His Met Gly Met Phe Thr Glu Leu Ala Ile Leu
        1310                1315                1320

Tyr Ser Lys Phe Lys Pro Gln Lys Met Arg Glu His Leu Glu Leu
        1325                1330                1335

Phe Trp Ser Arg Val Asn Ile Pro Lys Val Leu Arg Ala Ala Glu
        1340                1345                1350

Gln Ala His Leu Trp Ala Glu Leu Val Phe Leu Tyr Asp Lys Tyr
        1355                1360                1365
```

```
Glu Glu Tyr Asp Asn Ala Ile Ile Thr Met Met Asn His Pro Thr
    1370                1375                1380

Asp Ala Trp Lys Glu Gly Gln Phe Lys Asp Ile Ile Thr Lys Val
    1385                1390                1395

Ala Asn Val Glu Leu Tyr Tyr Arg Ala Ile Gln Phe Tyr Leu Glu
    1400                1405                1410

Phe Lys Pro Leu Leu Leu Asn Asp Leu Leu Met Val Leu Ser Pro
    1415                1420                1425

Arg Leu Asp His Thr Arg Ala Val Asn Tyr Phe Ser Lys Val Lys
    1430                1435                1440

Gln Leu Pro Leu Val Lys Pro Tyr Leu Arg Ser Val Gln Asn His
    1445                1450                1455

Asn Asn Lys Ser Val Asn Glu Ser Leu Asn Asn Leu Phe Ile Thr
    1460                1465                1470

Glu Glu Asp Tyr Gln Ala Leu Arg Thr Ser Ile Asp Ala Tyr Asp
    1475                1480                1485

Asn Phe Asp Asn Ile Ser Leu Ala Gln Arg Leu Glu Lys His Glu
    1490                1495                1500

Leu Ile Glu Phe Arg Arg Ile Ala Ala Tyr Leu Phe Lys Gly Asn
    1505                1510                1515

Asn Arg Trp Lys Gln Ser Val Glu Leu Cys Lys Lys Asp Ser Leu
    1520                1525                1530

Tyr Lys Asp Ala Met Gln Tyr Ala Ser Glu Ser Lys Asp Thr Glu
    1535                1540                1545

Leu Ala Glu Glu Leu Leu Gln Trp Phe Leu Gln Glu Glu Lys Arg
    1550                1555                1560

Glu Cys Phe Gly Ala Cys Leu Phe Thr Cys Tyr Asp Leu Leu Arg
    1565                1570                1575

Pro Asp Val Val Leu Glu Thr Ala Trp Arg His Asn Ile Met Asp
    1580                1585                1590

Phe Ala Met Pro Tyr Phe Ile Gln Val Met Lys Glu Tyr Leu Thr
    1595                1600                1605

Lys Val Asp Lys Leu Asp Ala Ser Glu Ser Leu Arg Lys Glu Glu
    1610                1615                1620

Glu Gln Ala Thr Glu Thr Gln Pro Ile Val Tyr Gly Gln Pro Gln
    1625                1630                1635

Leu Met Leu Thr Ala Gly Pro Ser Val Ala Val Pro Pro Gln Ala
    1640                1645                1650

Pro Phe Gly Tyr Gly Tyr Thr Ala Pro Pro Tyr Gly Gln Pro Gln
    1655                1660                1665

Pro Gly Phe Gly Tyr Ser Met
    1670                1675

<210> SEQ ID NO 3
<211> LENGTH: 575
<212> TYPE: PRT
<213> ORGANISM: rattus norvegicus

<400> SEQUENCE: 3

Met Ser Thr Ser Ser Leu Arg Arg Gln Met Lys Asn Ile Val His Asn
1               5                   10                  15

Tyr Ser Glu Ala Glu Ile Lys Val Arg Glu Ala Thr Ser Asn Asp Pro
                20                  25                  30

Trp Gly Pro Ser Ser Ser Leu Met Ser Glu Ile Ala Asp Leu Thr Tyr
            35                  40                  45
```

-continued

```
Asn Val Val Ala Phe Ser Glu Ile Met Ser Met Ile Trp Lys Arg Leu
 50              55                  60

Asn Asp His Gly Lys Asn Trp Arg His Val Tyr Lys Ala Met Thr Leu
 65              70                  75                  80

Met Glu Tyr Leu Ile Lys Thr Gly Ser Glu Arg Val Ser Gln Gln Cys
                 85                  90                  95

Lys Glu Asn Met Tyr Ala Val Gln Thr Leu Lys Asp Phe Gln Tyr Val
                100                 105                 110

Asp Arg Asp Gly Lys Asp Gln Gly Val Asn Val Arg Glu Lys Ala Lys
                115                 120                 125

Gln Leu Val Ala Leu Leu Arg Asp Glu Asp Arg Leu Arg Glu Glu Arg
130                 135                 140

Ala His Ala Leu Lys Thr Lys Glu Lys Leu Ala Gln Thr Ala Thr Ala
145                 150                 155                 160

Ser Ser Ala Ala Val Gly Ser Gly Pro Pro Pro Glu Ala Glu Gln Ala
                165                 170                 175

Trp Pro Gln Ser Ser Gly Glu Glu Glu Leu Gln Leu Gln Leu Ala Leu
                180                 185                 190

Ala Met Ser Lys Glu Glu Ala Asp Gln Pro Pro Ser Cys Gly Pro Glu
                195                 200                 205

Asp Val Gln Leu Gln Leu Ala Leu Ser Leu Ser Arg Glu Glu His
                210                 215                 220

Asp Lys Glu Glu Arg Ile Arg Arg Gly Asp Leu Arg Leu Gln Met
225                 230                 235                 240

Ala Ile Glu Glu Ser Lys Arg Glu Thr Gly Gly Lys Glu Glu Ser Ser
                245                 250                 255

Leu Met Asp Leu Ala Asp Val Phe Thr Thr Pro Ala Pro Pro Gln Ala
                260                 265                 270

Ser Asp Pro Trp Gly Pro Ala Ser Val Pro Thr Ala Val Pro Val
                275                 280                 285

Ala Ala Ala Ala Ser Asp Pro Trp Gly Ala Pro Ala Val Pro Pro Ala
290                 295                 300

Ala Asp Pro Trp Gly Gly Ala Pro Thr Pro Ala Ser Gly Asp Pro
305                 310                 315                 320

Trp Arg Pro Ala Ala Pro Thr Gly Pro Ser Val Asp Pro Trp Gly Gly
                325                 330                 335

Thr Pro Ala Pro Ala Ala Gly Glu Gly Pro Thr Ser Pro Trp Gly
                340                 345                 350

Ser Ala Asp Gly Gly Ala Pro Val Ser Gly Pro Pro Ser Ser Asp Pro
                355                 360                 365

Trp Ala Pro Ala Pro Ala Phe Ser Asp Pro Trp Gly Gly Ser Pro Ala
                370                 375                 380

Lys Pro Ser Ser Asn Gly Thr Ala Val Gly Gly Phe Asp Thr Glu Pro
385                 390                 395                 400

Asp Glu Phe Ser Asp Phe Asp Arg Leu Arg Thr Ala Leu Pro Thr Ser
                405                 410                 415

Gly Ser Ser Thr Gly Glu Leu Glu Leu Leu Ala Gly Glu Val Pro Ala
                420                 425                 430

Arg Ser Pro Gly Ala Phe Asp Met Ser Gly Val Gly Gly Ser Leu Ala
                435                 440                 445

Glu Ser Val Gly Ser Pro Pro Pro Ala Ala Thr Pro Thr Pro Thr Pro
450                 455                 460
```

```
Pro Thr Arg Lys Thr Pro Glu Ser Phe Leu Gly Pro Asn Ala Ala Leu
465                 470                 475                 480

Val Asp Leu Asp Ser Leu Val Ser Arg Pro Gly Pro Thr Pro Pro Gly
                485                 490                 495

Ala Lys Ala Ser Asn Pro Phe Leu Pro Ser Gly Ala Pro Ala Thr Gly
                500                 505                 510

Pro Ser Val Thr Asn Pro Phe Gln Pro Ala Pro Pro Ala Thr Leu Thr
                515                 520                 525

Leu Asn Gln Leu Arg Leu Ser Pro Val Pro Pro Val Pro Gly Ala Pro
                530                 535                 540

Pro Thr Tyr Ile Ser Pro Leu Gly Gly Gly Pro Gly Leu Pro Pro Met
545                 550                 555                 560

Met Pro Pro Gly Pro Pro Ala Pro Asn Thr Asn Pro Phe Leu Leu
                565                 570                 575

<210> SEQ ID NO 4
<211> LENGTH: 144
<212> TYPE: PRT
<213> ORGANISM: rattus norvegicus

<400> SEQUENCE: 4

Met Ser Thr Ser Ser Leu Arg Arg Gln Met Lys Asn Ile Val His Asn
1               5                   10                  15

Tyr Ser Glu Ala Glu Ile Lys Val Arg Glu Ala Thr Ser Asn Asp Pro
                20                  25                  30

Trp Gly Pro Ser Ser Ser Leu Met Ser Glu Ile Ala Asp Leu Thr Tyr
                35                  40                  45

Asn Val Val Ala Phe Ser Glu Ile Met Ser Met Ile Trp Lys Arg Leu
50                  55                  60

Asn Asp His Gly Lys Asn Trp Arg His Val Tyr Lys Ala Met Thr Leu
65                  70                  75                  80

Met Glu Tyr Leu Ile Lys Thr Gly Ser Glu Arg Val Ser Gln Gln Cys
                85                  90                  95

Lys Glu Asn Met Tyr Ala Val Gln Thr Leu Lys Asp Phe Gln Tyr Val
                100                 105                 110

Asp Arg Asp Gly Lys Asp Gln Gly Val Asn Val Arg Glu Lys Ala Lys
                115                 120                 125

Gln Leu Val Ala Leu Leu Arg Asp Glu Asp Arg Leu Arg Glu Glu Arg
                130                 135                 140

<210> SEQ ID NO 5
<211> LENGTH: 228
<212> TYPE: PRT
<213> ORGANISM: bos taurus

<400> SEQUENCE: 5

Met Ala Asp Asp Phe Gly Phe Phe Ser Ser Ser Glu Ser Gly Ala Pro
1               5                   10                  15

Glu Ala Ala Glu Glu Asp Pro Ala Ala Ala Phe Leu Ala Gln Gln Glu
                20                  25                  30

Ser Glu Ile Ala Gly Ile Glu Asn Asp Glu Gly Phe Gly Ala Pro Ala
                35                  40                  45

Gly Ser Gln Gly Gly Leu Ala Gln Pro Gly Pro Ala Ser Gly Ala Ser
                50                  55                  60

Glu Asp Met Gly Ala Thr Val Asn Gly Asp Val Phe Gln Glu Ala Asn
65                  70                  75                  80
```

Gly Pro Ala Asp Gly Tyr Ala Ala Ile Ala Gln Ala Asp Arg Leu Thr
            85                  90                  95

Gln Glu Pro Glu Ser Ile Arg Lys Trp Arg Glu Glu Gln Arg Lys Arg
        100                 105                 110

Leu Gln Glu Leu Asp Ala Ala Ser Lys Val Met Glu Gln Glu Trp Arg
        115                 120                 125

Glu Lys Ala Lys Lys Asp Leu Glu Glu Trp Asn Gln Arg Gln Ser Glu
130                 135                 140

Gln Val Glu Lys Asn Lys Ile Asn Asn Arg Ile Ala Asp Lys Ala Phe
145                 150                 155                 160

Tyr Gln Gln Pro Asp Ala Asp Ile Ile Gly Tyr Val Ala Ser Glu Glu
                165                 170                 175

Ala Phe Val Lys Glu Ser Lys Glu Glu Thr Pro Gly Thr Glu Trp Glu
        180                 185                 190

Lys Val Ala Gln Leu Cys Asp Phe Asn Pro Lys Ser Ser Lys Gln Cys
        195                 200                 205

Lys Asp Val Ser Arg Leu Arg Ser Val Leu Met Ser Leu Lys Gln Thr
210                 215                 220

Pro Leu Ser Arg
225

<210> SEQ ID NO 6
<211> LENGTH: 175
<212> TYPE: PRT
<213> ORGANISM: sus scrofa

<400> SEQUENCE: 6

Met Ala Asp Asp Phe Gly Phe Phe Ser Ser Glu Ser Gly Ala Pro
1               5                   10                  15

Glu Val Ala Glu Glu Asp Pro Ala Ala Ala Phe Leu Ala Gln Gln Glu
            20                  25                  30

Ser Glu Ile Ala Gly Ile Glu Asn Asp Glu Gly Phe Gly Ala Pro Ala
        35                  40                  45

Gly Ser Gln Ala Ala Leu Ala Gln Pro Gly Pro Ala Ser Gly Ala Gly
    50                  55                  60

Pro Glu Asp Met Gly Thr Thr Val Asn Gly Asp Val Phe Gln Asp Ala
65                  70                  75                  80

Asn Gly Pro Ala Asp Gly Tyr Ala Ala Ile Ala Gln Ala Asp Arg Leu
                85                  90                  95

Thr Gln Glu Pro Glu Ser Ile Arg Lys Trp Arg Glu Glu Gln Arg Lys
            100                 105                 110

Arg Leu Gln Glu Leu Asp Ala Ala Ser Lys Val Thr Glu Gln Glu Trp
        115                 120                 125

Arg Glu Lys Ala Lys Lys Asp Leu Glu Glu Trp Asn Gln Arg Gln Ser
    130                 135                 140

Glu Gln Val Glu Lys Asn Lys Ile Asn Asn Arg Ile Ala Asp Lys Ala
145                 150                 155                 160

Phe Tyr Gln Gln Pro Asp Ala Asp Ile Ile Gly Tyr Val Ala Ser
                165                 170                 175

<210> SEQ ID NO 7
<211> LENGTH: 851
<212> TYPE: PRT
<213> ORGANISM: human

<400> SEQUENCE: 7

```
Met Gly Asn Arg Gly Met Glu Asp Leu Ile Pro Leu Val Asn Arg Leu
1               5                   10                  15

Gln Asp Ala Phe Ser Ala Ile Gly Gln Asn Ala Asp Leu Asp Leu Pro
            20                  25                  30

Gln Ile Ala Val Val Gly Gly Gln Ser Ala Gly Lys Ser Ser Val Leu
        35                  40                  45

Glu Asn Phe Val Gly Arg Asp Phe Leu Pro Arg Gly Ser Gly Ile Val
    50                  55                  60

Thr Arg Arg Pro Leu Val Leu Gln Leu Val Asn Ala Thr Thr Glu Tyr
65                  70                  75                  80

Ala Glu Phe Leu His Cys Lys Gly Lys Lys Phe Thr Asp Phe Glu Glu
                85                  90                  95

Val Arg Leu Glu Ile Glu Ala Glu Thr Asp Arg Val Thr Gly Thr Asn
            100                 105                 110

Lys Gly Ile Ser Pro Val Pro Ile Asn Leu Arg Val Tyr Ser Pro His
        115                 120                 125

Val Leu Asn Leu Thr Leu Val Asp Leu Pro Gly Met Thr Lys Val Pro
    130                 135                 140

Val Gly Asp Gln Pro Pro Asp Ile Glu Phe Gln Ile Arg Asp Met Leu
145                 150                 155                 160

Met Gln Phe Val Thr Lys Glu Asn Cys Leu Ile Leu Ala Val Ser Pro
                165                 170                 175

Ala Asn Ser Asp Leu Ala Asn Ser Asp Ala Leu Glu Val Ala Lys Glu
            180                 185                 190

Val Asp Pro Gln Gly Gln Arg Thr Ile Gly Val Ile Thr Lys Leu Asp
        195                 200                 205

Leu Met Asp Glu Gly Thr Asp Ala Arg Asp Val Leu Glu Asn Lys Leu
    210                 215                 220

Leu Pro Leu Arg Arg Gly Tyr Ile Gly Val Val Asn Arg Ser Gln Lys
225                 230                 235                 240

Asp Ile Asp Gly Lys Lys Asp Ile Thr Ala Ala Leu Ala Ala Glu Arg
                245                 250                 255

Lys Phe Phe Leu Ser His Pro Ser Tyr Arg His Leu Ala Asp Arg Met
            260                 265                 270

Gly Thr Pro Tyr Leu Gln Lys Val Leu Asn Gln Gln Leu Thr Asp His
        275                 280                 285

Ile Arg Asp Thr Leu Pro Gly Leu Arg Asn Lys Leu Gln Ser Gln Leu
    290                 295                 300

Leu Ser Ile Glu Lys Glu Val Glu Glu Tyr Lys Asn Phe Arg Pro Asp
305                 310                 315                 320

Asp Pro Ala Arg Lys Thr Lys Ala Leu Leu Gln Met Val Gln Gln Phe
                325                 330                 335

Ala Val Asp Phe Glu Lys Arg Ile Glu Gly Ser Gly Asp Gln Ile Asp
            340                 345                 350

Thr Tyr Glu Leu Ser Gly Gly Ala Arg Ile Asn Arg Ile Phe His Glu
        355                 360                 365

Arg Phe Pro Phe Glu Leu Val Lys Met Glu Phe Asp Glu Lys Glu Leu
    370                 375                 380

Arg Arg Glu Ile Ser Tyr Ala Ile Lys Asn Ile His Gly Ile Arg Thr
385                 390                 395                 400

Gly Leu Phe Thr Pro Asp Met Ala Phe Glu Thr Ile Val Lys Lys Gln
                405                 410                 415
```

-continued

```
Val Lys Lys Ile Arg Glu Pro Cys Leu Lys Cys Val Asp Met Val Ile
            420                 425                 430
Ser Glu Leu Ile Ser Thr Val Arg Gln Cys Thr Lys Lys Leu Gln Gln
        435                 440                 445
Tyr Pro Arg Leu Arg Glu Glu Met Glu Arg Ile Val Thr Thr His Ile
    450                 455                 460
Arg Glu Arg Glu Gly Arg Thr Lys Glu Gln Val Met Leu Leu Ile Asp
465                 470                 475                 480
Ile Glu Leu Ala Tyr Met Asn Thr Asn His Glu Asp Phe Ile Gly Phe
                485                 490                 495
Ala Asn Ala Gln Gln Arg Ser Asn Gln Met Asn Lys Lys Lys Thr Ser
            500                 505                 510
Gly Asn Gln Asp Glu Ile Leu Val Ile Arg Lys Gly Trp Leu Thr Ile
        515                 520                 525
Asn Asn Ile Gly Ile Met Lys Gly Gly Ser Lys Glu Tyr Trp Phe Val
    530                 535                 540
Leu Thr Ala Glu Asn Leu Ser Trp Tyr Lys Asp Asp Glu Glu Lys Glu
545                 550                 555                 560
Lys Lys Tyr Met Leu Ser Val Asp Asn Leu Lys Leu Arg Asp Val Glu
                565                 570                 575
Lys Gly Phe Met Ser Ser Lys His Ile Phe Ala Leu Phe Asn Thr Glu
            580                 585                 590
Gln Arg Asn Val Tyr Lys Asp Tyr Arg Gln Leu Glu Leu Ala Cys Glu
        595                 600                 605
Thr Gln Glu Glu Val Asp Ser Trp Lys Ala Ser Phe Leu Arg Ala Gly
    610                 615                 620
Val Tyr Pro Glu Arg Val Gly Asp Lys Glu Lys Ala Ser Glu Thr Glu
625                 630                 635                 640
Glu Asn Gly Ser Asp Ser Phe Met His Ser Met Asp Pro Gln Leu Glu
                645                 650                 655
Arg Gln Val Glu Thr Ile Arg Asn Leu Val Asp Ser Tyr Met Ala Ile
            660                 665                 670
Val Asn Lys Thr Val Arg Asp Leu Met Pro Lys Thr Ile Met His Leu
        675                 680                 685
Met Ile Asn Asn Thr Lys Glu Phe Ile Phe Ser Glu Leu Leu Ala Asn
    690                 695                 700
Leu Tyr Ser Cys Gly Asp Gln Asn Thr Leu Met Glu Glu Ser Ala Glu
705                 710                 715                 720
Gln Ala Gln Arg Arg Asp Glu Met Leu Arg Met Tyr His Ala Leu Lys
                725                 730                 735
Glu Ala Leu Ser Ile Ile Gly Asp Ile Asn Thr Thr Thr Val Ser Thr
            740                 745                 750
Pro Met Pro Pro Pro Val Asp Asp Ser Trp Leu Gln Val Gln Ser Val
        755                 760                 765
Pro Ala Gly Arg Arg Ser Pro Thr Ser Ser Pro Thr Pro Gln Arg Arg
    770                 775                 780
Ala Pro Ala Val Pro Pro Ala Arg Pro Gly Ser Arg Gly Pro Ala Pro
785                 790                 795                 800
Gly Pro Pro Pro Ala Gly Ser Ala Met Gly Gly Ala Pro Pro Val Pro
                805                 810                 815
Ser Arg Pro Gly Ala Ser Pro Asp Pro Phe Gly Pro Pro Pro Gln Val
            820                 825                 830
```

-continued

```
Pro Ser Arg Pro Asn Arg Ala Pro Pro Gly Val Pro Arg Ile Thr Ile
        835                 840                 845

Ser Asp Pro
    850

<210> SEQ ID NO 8
<211> LENGTH: 851
<212> TYPE: PRT
<213> ORGANISM: sus scrofa

<400> SEQUENCE: 8

Met Gly Asn Arg Gly Met Glu Asp Leu Ile Pro Leu Val Asn Arg Leu
1               5                   10                  15

Gln Asp Ala Phe Ser Ala Ile Gly Gln Asn Ala Asp Leu Asp Leu Pro
            20                  25                  30

Gln Ile Ala Val Val Gly Gly Gln Ser Ala Gly Lys Ser Ser Val Leu
        35                  40                  45

Glu Asn Phe Val Gly Arg Asp Phe Leu Pro Arg Gly Ser Gly Ile Val
    50                  55                  60

Thr Arg Arg Pro Leu Val Leu Gln Leu Val Asn Ala Thr Thr Glu Tyr
65                  70                  75                  80

Ala Glu Phe Leu His Cys Lys Gly Lys Lys Phe Thr Asp Phe Glu Glu
                85                  90                  95

Val Arg Leu Glu Ile Glu Ala Glu Thr Asp Arg Val Thr Gly Thr Asn
            100                 105                 110

Lys Gly Ile Ser Pro Val Pro Ile Asn Leu Arg Val Tyr Ser Pro His
        115                 120                 125

Val Leu Asn Leu Thr Leu Val Asp Leu Pro Gly Met Thr Lys Val Pro
    130                 135                 140

Val Gly Asp Gln Pro Pro Asp Ile Glu Phe Gln Ile Arg Asp Met Leu
145                 150                 155                 160

Met Gln Phe Val Thr Lys Glu Asn Cys Leu Ile Leu Ala Val Ser Pro
                165                 170                 175

Ala Asn Ser Asp Leu Ala Asn Ser Asp Ala Leu Lys Val Ala Lys Glu
            180                 185                 190

Val Asp Pro Gln Gly Gln Arg Thr Ile Gly Val Ile Thr Lys Leu Asp
        195                 200                 205

Leu Met Asp Glu Gly Thr Asp Ala Arg Asp Val Leu Glu Asn Lys Leu
    210                 215                 220

Leu Pro Leu Arg Arg Gly Tyr Ile Gly Val Val Asn Arg Ser Gln Lys
225                 230                 235                 240

Asp Ile Asp Gly Lys Lys Asp Ile Thr Ala Ala Leu Ala Ala Glu Arg
                245                 250                 255

Lys Phe Phe Leu Ser His Pro Ser Tyr Arg His Leu Ala Asp Arg Met
            260                 265                 270

Gly Thr Pro Tyr Leu Gln Lys Val Leu Asn Gln Gln Leu Thr Asn His
        275                 280                 285

Ile Arg Asp Thr Leu Pro Gly Leu Arg Asn Lys Leu Gln Ser Gln Leu
    290                 295                 300

Leu Ser Ile Glu Lys Glu Val Glu Glu Tyr Lys Asn Phe Arg Pro Asp
305                 310                 315                 320

Asp Pro Ala Arg Lys Thr Lys Ala Leu Leu Gln Met Val Gln Gln Phe
                325                 330                 335

Ala Val Asp Phe Glu Lys Arg Ile Glu Gly Ser Gly Asp Gln Ile Asp
            340                 345                 350
```

-continued

```
Thr Tyr Glu Leu Ser Gly Gly Ala Arg Ile Asn Arg Ile Phe His Glu
            355                 360                 365
Arg Phe Pro Phe Glu Leu Val Lys Met Glu Phe Asp Glu Lys Glu Leu
        370                 375                 380
Arg Arg Glu Ile Ser Tyr Ala Ile Lys Asn Ile His Gly Ile Arg Thr
385                 390                 395                 400
Gly Leu Phe Thr Pro Asp Met Ala Phe Glu Thr Ile Val Lys Lys Gln
                405                 410                 415
Val Lys Lys Ile Arg Glu Pro Cys Leu Lys Cys Val Asp Met Val Ile
            420                 425                 430
Ser Glu Leu Ile Ser Thr Val Arg Gln Cys Thr Lys Lys Leu Gln Gln
        435                 440                 445
Tyr Pro Arg Leu Arg Glu Glu Met Glu Arg Ile Val Thr Thr His Ile
    450                 455                 460
Arg Glu Arg Glu Gly Arg Thr Lys Glu Gln Val Met Leu Leu Ile Asp
465                 470                 475                 480
Ile Glu Leu Ala Tyr Met Asn Thr Asn His Glu Asp Phe Ile Gly Phe
                485                 490                 495
Ala Asn Ala Gln Gln Arg Ser Asn Gln Met Asn Lys Lys Lys Ala Ser
            500                 505                 510
Gly Asn Gln Asp Glu Ile Leu Val Ile Arg Lys Gly Trp Leu Thr Ile
        515                 520                 525
Asn Asn Ile Gly Ile Met Lys Gly Gly Ser Lys Glu Tyr Trp Phe Val
    530                 535                 540
Leu Thr Ala Glu Asn Leu Ser Trp Tyr Lys Asp Asp Glu Glu Lys Glu
545                 550                 555                 560
Lys Lys Tyr Met Leu Ser Val Asp Asn Leu Lys Leu Arg Asp Val Glu
                565                 570                 575
Lys Gly Phe Met Ser Ser Lys His Ile Phe Ala Leu Phe Asn Thr Glu
            580                 585                 590
Gln Arg Asn Val Tyr Lys Asp Tyr Arg Gln Leu Glu Leu Ala Cys Glu
        595                 600                 605
Thr Gln Glu Glu Val Asp Ser Trp Lys Ala Ser Phe Leu Arg Ala Gly
    610                 615                 620
Val Tyr Pro Glu Arg Val Gly Asp Lys Glu Lys Ala Ser Glu Thr Glu
625                 630                 635                 640
Glu Asn Gly Ser Asp Ser Phe Met His Ser Met Asp Pro Gln Leu Glu
                645                 650                 655
Arg Gln Val Glu Thr Ile Arg Asn Leu Val Asp Ser Tyr Met Ala Ile
            660                 665                 670
Val Asn Lys Thr Val Arg Asp Leu Met Pro Lys Thr Ile Met His Leu
        675                 680                 685
Met Ile Asn Asn Thr Lys Glu Phe Ile Phe Ser Glu Leu Leu Ala Asn
    690                 695                 700
Leu Tyr Ser Cys Gly Asp Gln Asn Thr Leu Met Glu Glu Ser Ala Glu
705                 710                 715                 720
Gln Ala Gln Arg Arg Asp Glu Met Leu Arg Met Tyr His Ala Leu Lys
                725                 730                 735
Glu Ala Leu Ser Ile Ile Gly Asp Ile Asn Thr Thr Val Ser Thr
            740                 745                 750
Pro Met Pro Pro Val Asp Asp Ser Trp Leu Gln Val Gln Ser Ile
        755                 760                 765
```

-continued

```
Pro Ala Gly Arg Arg Ser Pro Thr Ser Ser Pro Thr Pro Gln Arg Arg
    770             775             780

Ala Pro Ala Val Pro Pro Ala Arg Pro Gly Ser Arg Gly Pro Ala Pro
785             790             795                         800

Gly Pro Pro Pro Ala Gly Ser Ala Leu Gly Gly Ala Pro Pro Val Pro
            805             810                     815

Ser Arg Pro Gly Ala Ser Pro Asp Pro Phe Gly Pro Pro Pro Gln Val
            820             825                 830

Pro Ser Arg Pro Asn Arg Ala Pro Pro Gly Val Pro Arg Ile Thr Ile
        835             840             845

Ser Asp Pro
    850
```